United States Patent
Aprahamian et al.

(10) Patent No.: US 6,393,315 B1
(45) Date of Patent: May 21, 2002

(54) DETECTING AND MAPPING OF INFLAMED ZONES IN A LIVING TISSUE

(75) Inventors: Pierre Marc Aprahamian, Limersheim; Francine Heisel, Strasbourg, both of (FR); Alfredo Lucia, Osmate (IT); Joseph-Albert Miehe, Strasbourg; Malgorzata Sowinska, Ittenheim, both of (FR); Maurice Whelan, Ranco (IT)

(73) Assignee: Communaute Europeenne, Luxembourg (LU)

( * ) Notice: Subject to any disclaimer, the term of this patent is extended or adjusted under 35 U.S.C. 154(b) by 0 days.

(21) Appl. No.: 09/508,408

(22) PCT Filed: Sep. 11, 1998

(86) PCT No.: PCT/FR98/01950

§ 371 Date: Apr. 5, 2000

§ 102(e) Date: Apr. 5, 2000

(87) PCT Pub. No.: WO99/13764

PCT Pub. Date: Mar. 25, 1999

(30) Foreign Application Priority Data

Sep. 12, 1997 (FR) .............................................. 97 11534

(51) Int. Cl.[7] ................................................. A61B 6/00
(52) U.S. Cl. ........................ 600/476; 382/128; 356/402; 356/403; 356/432; 606/2
(58) Field of Search ................................. 600/310, 312, 600/473, 476; 382/128; 606/1, 2, 3; 607/1, 88, 89, 91, 9.2; 356/51, 345, 346, 300, 402, 403, 432, 213

(56) References Cited

U.S. PATENT DOCUMENTS

| | | | |
|---|---|---|---|
| 4,930,516 A | | 6/1990 | Alfano et al. |
| 5,201,318 A | | 4/1993 | Rava et al. |
| 5,377,676 A | * | 1/1995 | Vari et al. .................... 128/634 |
| 5,419,323 A | * | 5/1995 | Kittrell et al. ........... 128/653.1 |
| 5,760,407 A | * | 6/1998 | Margosiak et al. ...... 250/461.1 |
| 6,083,485 A | * | 7/2000 | Licha et al. ................. 424/9.6 |

FOREIGN PATENT DOCUMENTS

EP   0 512 965   11/1992

OTHER PUBLICATIONS

By Jianan Qu et al., "Laser–induced fluorescence spectros-–copy at endoscopy: tissue optics, Monte Carlo modeling, and in vivo measurements", Optical Engineering, vol. 34, No. 11, Nov. 1995, pp. 3334–3343.

Dong Yang et al., "A method for clinical detection of cancer by rapidly analyzing the argon laser induced autofluorescence spectra", Proceedings of the SPIE, vol. 1616, Oct. 15, 1991, pp. 82–89.

* cited by examiner

Primary Examiner—Marvin M. Lateef
Assistant Examiner—Jeoyuh Lin
(74) Attorney, Agent, or Firm—Young & Thompson

(57) ABSTRACT

A method for detecting and mapping inflamed zones in living tissues and a device for implementing the method. The method includes subjecting the tissues to be analyzed to a luminous excitation with a predetermined spectral domain, acquiring at least the raw fluorescence signal of the porphyrins for a plurality of measurement points, and in determining, for each measurement point, the intensity of the fluorescence for the wavelengths characteristic of endogenous porphyrins.

18 Claims, 7 Drawing Sheets

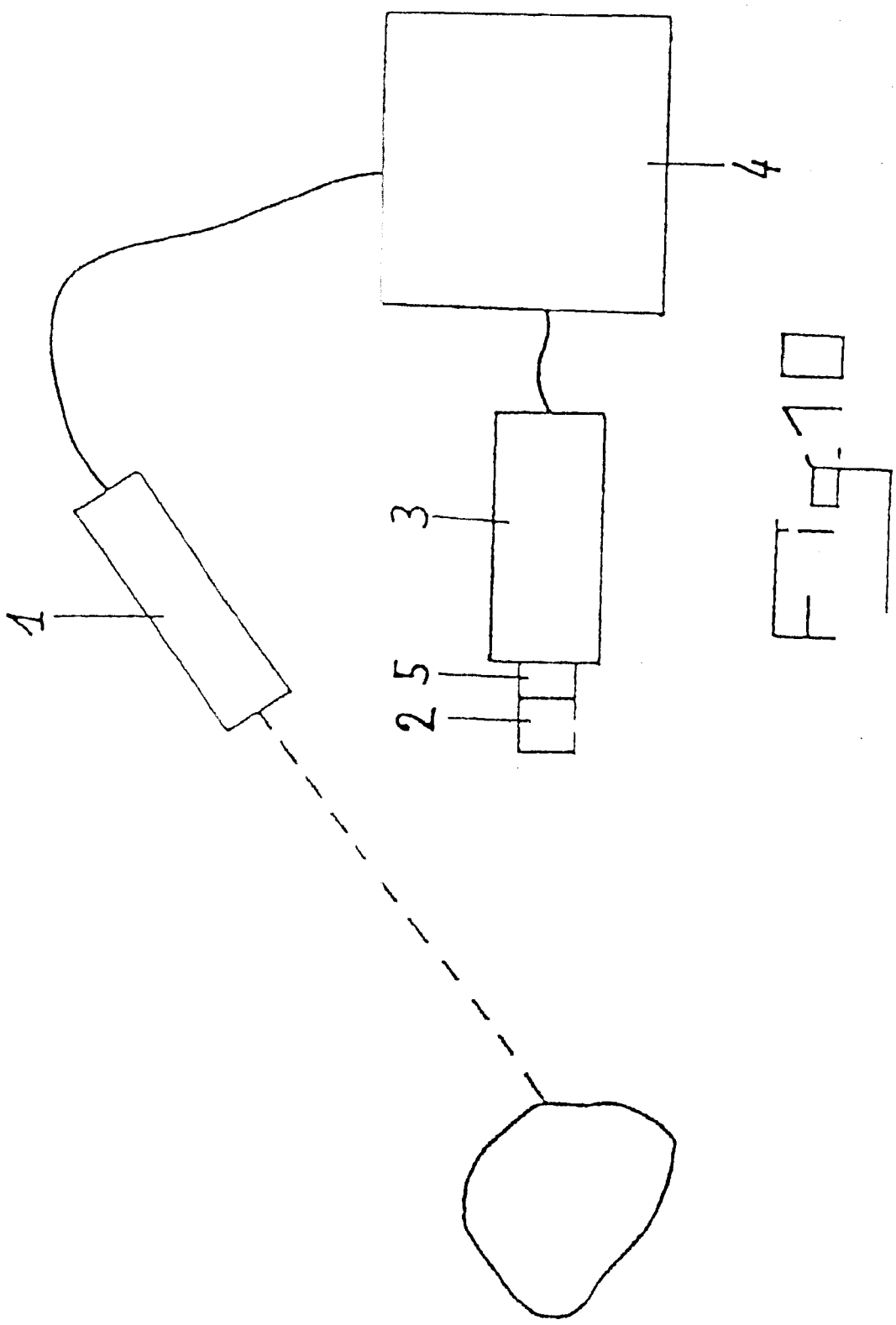

DETECTING AND MAPPING OF INFLAMED ZONES IN A LIVING TISSUE

CROSS REFERENCE TO RELATED APPLICATION

This is the 35 USC 371 national stage of International Application PCT/FR98/01950 filed on Sep. 11, 1998 which designated the United States of America.

FIELD OF THE INVENTION

The present invention relates to the field of examination and analysis of living tissues, and has for its object a process for the detection and mapping of inflamed zones of living tissues, as well as a device to practice the same.

BACKGROUND OF THE INVENTION

The term "inflammation" generally designates, and particularly in the present case, all the processes developed by living organisms in response to an aggression of internal or external origin.

Inflammation gives rise to the major cellular histocompatibility system comprising leukocytes, lymphocytes, monocytes, histocytes, macrophages, etc . . . , as well as their secretion products such as prostaglandins, histamines, serotonins and cytokines (interferons, interleukins, tumoral necrosis factors . . . ).

It is already known to use the fluorescence of an exogensis chromophore of the type derived from hematoporphyrin or of the precursor type of protoporphyrine IX (5-amino-levulinic acid) to detect inflammatory or cancerous lesions.

Thus, it has been shown that these exogenous chromophores, concentrate, after injection, more particularly in the inflammatory or cancerous lesions.

Moreover, there are also known methods for the detection of cancers based on emission of autofluorescence in the spectral band of blue light.

In these latter methods, one takes account of the endogenous chromophores derived from nicotinamides (NAD, NADH), or constituting an extracellular matrix such as collagens, elastins or flavin derivatives.

Moreover, the presence of porphyrins in tissues has been known since 1920. It has been observed in tumors, and then in the Harder gland (located behind the eye muscles) of rodents and finally in very small quantity in normal tissues. It is principally protoporphyrin IX synthesized in cells from 5-amino-levulinic acid, that is the first step of the synthesis of hemoglobin.

The reason for the presence of this enzymatic path (normally expressed in the bone marrow) in normal or tumorous tissues, remains for the moment unknown, although it has recently been shown that this synthesis is under the control of certain hypophysary hormones.

SUMMARY OF THE INVENTION

However, the inventors of the present invention have discovered, in an unexpected and surprising manner, the presence of an abnormally high quantity of porphyrins in numerous situations whose common character is the existence of an inflammation. Present at very low levels in healthy tissues which have been studied (muscles, esophagus, pancreas and liver, at a slightly higher level in this latter, the site of partial destruction of the red corpuscles), these endogenous porphyrins become very abundant in these same tissues after aggression by a trauma (muscle), an irritating product (liver), by the development of a cancer (esophagus, pancreas) or an acute or chronic experimental pancreatitis.

The present invention has for its present object a process for the detection and mapping of inflamed zones of living tissues, characterized in that it consists in subjecting the tissues to be analyzed to a luminous excitation in a predetermined spectral field, acquiring at least the unprocessed fluorescence signal of the porphyrins for a plurality of points of measurement, and determining, for each point of measurement, at least the intensity of fluorescence for wavelengths characteristic of endogenous porphyrins.

The invention also has for its object a device for practicing the mentioned process, principally constituted by a luminous excitation unit of low intensity in the spectral bands centered about 400 nm and about 590 nm, a filtering module comprising a set of pass-band filters adapted to select fluorescenses specific to the different chromophores in question, a unit for detection and recordation of images of the fluorescence of the surface of the examined tissues and, finally, a data unit for processing point by point, or pixel by pixel, of the images recovered and the command and control of the assembly of the device, associated with storage and edition means for images.

BRIEF DESCRIPTION OF THE DRAWINGS

The invention will be better understood from the following description, which relates to a preferred embodiment, given by way of non-limiting example, and explained with reference to the accompanying schematic drawings, in which.

DETAILED DESCRIPTION OF THE INVENTION

Figure 1:
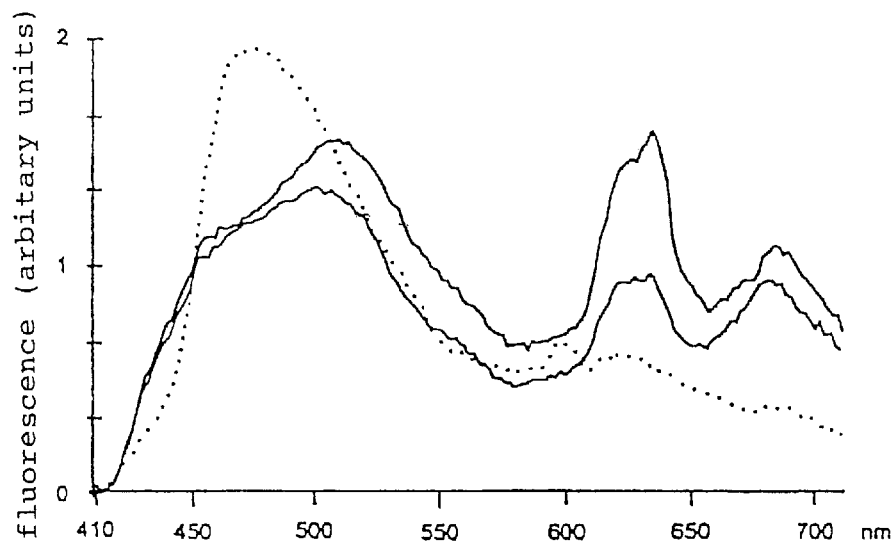
FIG. 1 shows the fluorescence spectra, on the one hand, of muscles in the course of healing (during the so-called "inflammatory" phase) and, on the other hand, of an undamaged muscle (broken line)
Figure 2:
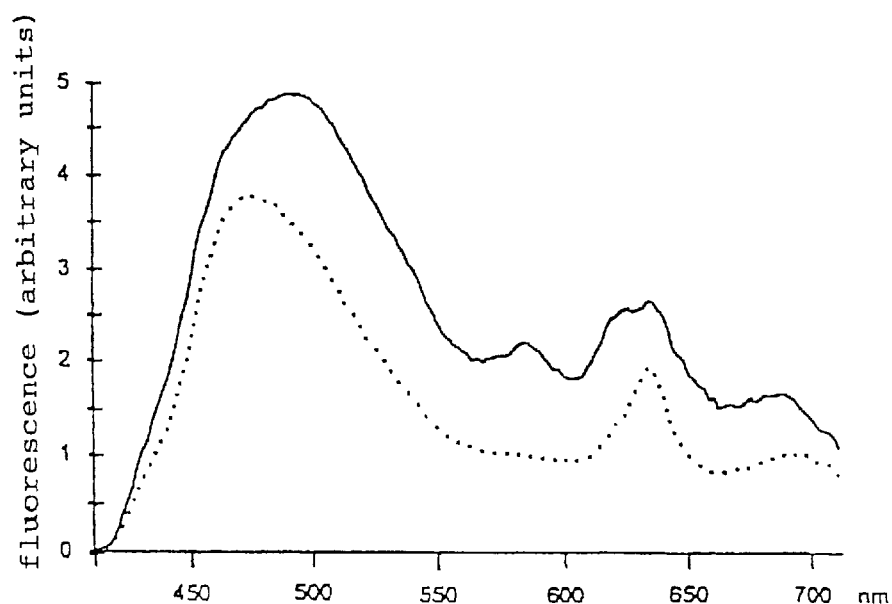
FIG. 2 shows the fluorescence spectra, on the one hand, of a liver injured by retrograde injection of taurocholate (to reproduce a hepatic type lesion) and, on the other hand, of an undamaged liver (in broken line)
Figure 3:
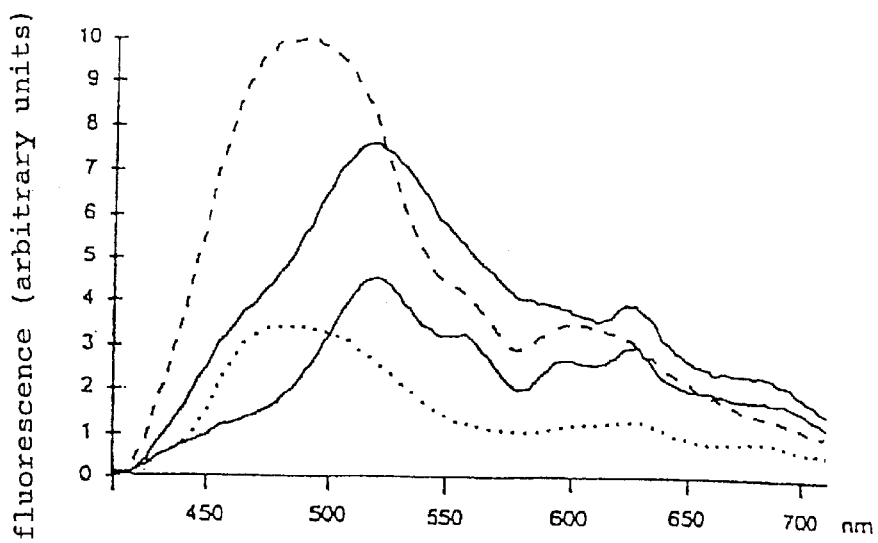
FIG. 3 shows the fluorescence spectra, on the one hand, of esophagi with adenocarcinomas, and, on the other hand, an undamaged esophagus (in fine broken line)

According to the invention, the process for the detection and mapping of inflamed zones of living tissues, consists essentially in subjecting the tissues to be analyzed to a luminous excitation with a predetermined spectral range, acquiring at least the unprocessed fluorescence signal of porphyrins for a plurality of measuring points, and determining, for each measurement point, the intensity of fluorescence for the wavelengths characteristic of endogenous porphyrins.

By endogenous porphyrins, the inventors mean porphyrins normally present in tissue without any exogenous addition, particularly without the addition of an external agent giving rise to an increase in the formation of porphyrins, such as for example δ-aminolevulinic acid (ALA) precursor of protoporphyrin IX.

FIGS. 1 to 7 show examples of the fluorescent spectra of different healthy tissues and of the same tissues having inflammations of various origins.

It should be noted that there can be seen, in all these spectra, a fluorescent emission band in the red (substantially comprised between 600 and 800 nm) of more or less high intensity and which systematically has two emission peaks that are easily recognizable, namely a principal peak at 630 nm and a secondary peak at 690 nm, this double peaking being characteristic of porphyrin fluorescence.

It will also be seen from these figures that in all the cases of inflammation shown, a maximum of the fluorescence band in the blue has an offset toward the green of about 50 nm.

Moreover, there has also been noticed, independently of the absolute value of fluorescence (very difficult to estimate for dense tissues), an increase of the ratio of the intensities of fluorescence emitted in the red (porphyrins) to those emitted in the blue (constituting the cellular matrix and extra cellular matrix), relative to a corresponding increase of the seriousness of inflammation.

This dependent relation indicates the existence of a direct correlation between, on the one hand, the concentration of porphyrins, and hence the value of the intensity of fluorescence for wavelengths characteristic of porphyrin and, on the other hand, the importance of the intensity of the inflamed lesions, permitting the gradation of inflammatory character of a tissue lesion.

This possibility of carrying out a gradation of the gravity of the inflammatory process has been verified by the inventors by comparison between the macroscopic phenomena observed in the autopsy of animals having pancreatitis and the measurements of fluorescence of the endogenous porphyrins carried out on the corresponding pancreases.

It will thus be seen that in the case of reduced pancreatitis (simple edema of the gland) this fluorescence is multiplied by two, in comparison to that of the normal or healthy pancreatic tissue. Severe pancreatitis, leading to death of the animal, with the autopsy of a necrotic pancreatic gland, is correlated to a fluorescence of the endogenous porphyrins five times higher than in the case of simple edemic pancreatitis.

Figure 4:
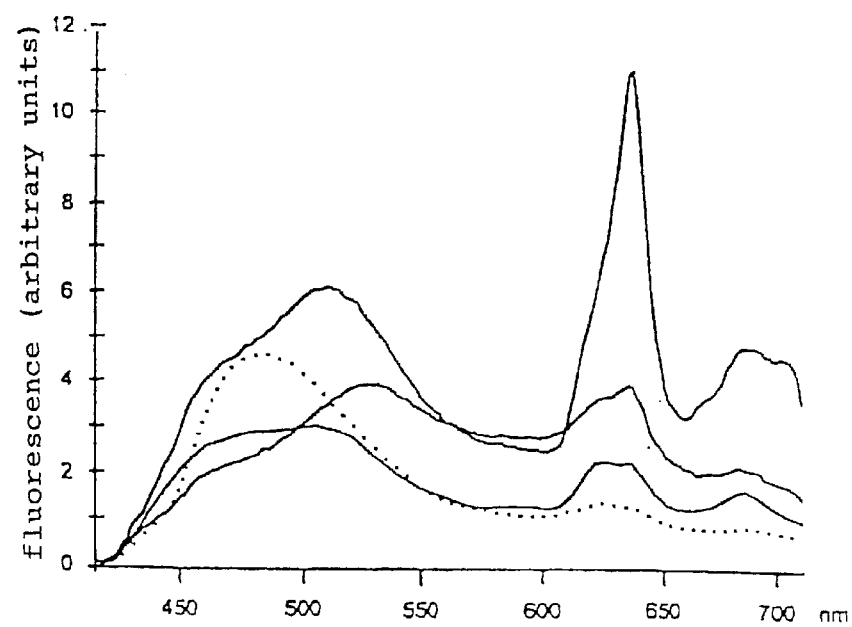
FIG. 4 shows the fluorescence spectra, on the one hand, of a pancreas having increasing stages of acute pancreatic necrotico-hemorrhage, and, on the other hand, an undamaged pancreas (in broken line)
Figure 5:
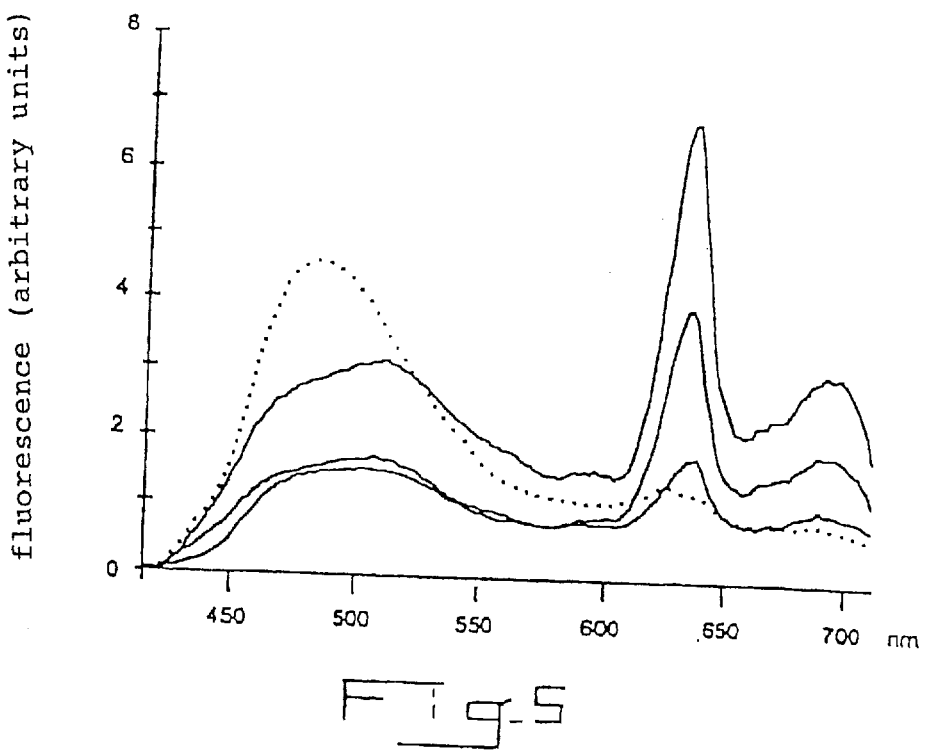
FIG. 5 shows the fluorescence spectra, on the one hand, of pancreases having adenocarcinomens of the ductal phenotype and, on the other hand, of an undamaged pancreas (in broken line)
Figure 6:
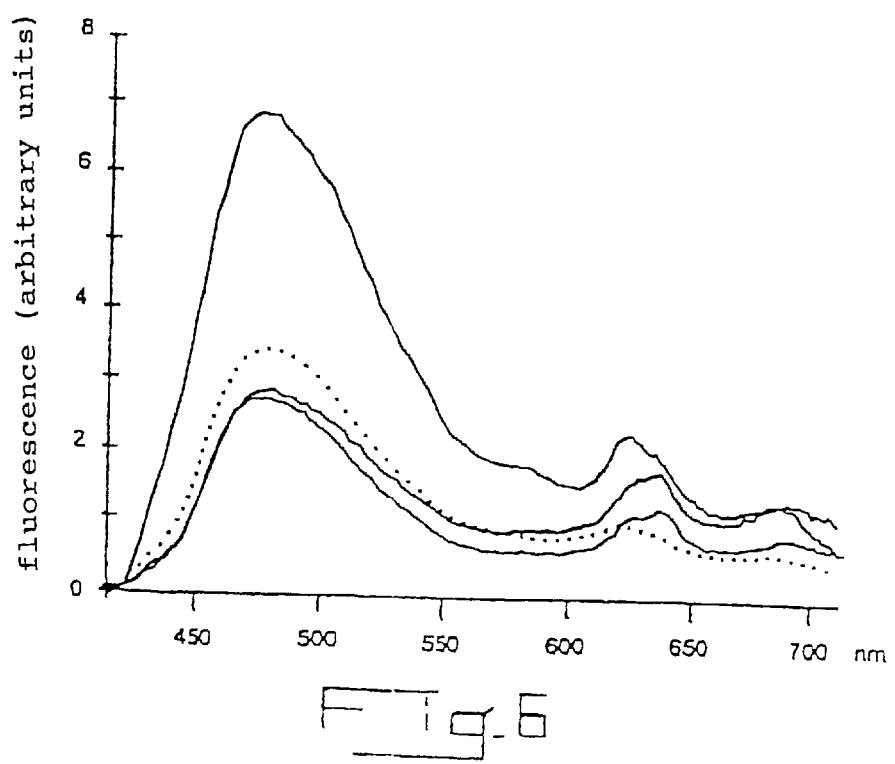
FIG. 6 shows the fluorescence spectra, on the one hand, of healthy regions of a pancreas having adenocarcinomas and, on the other hand, an undamaged pancreas (in broken line)
Figure 7:
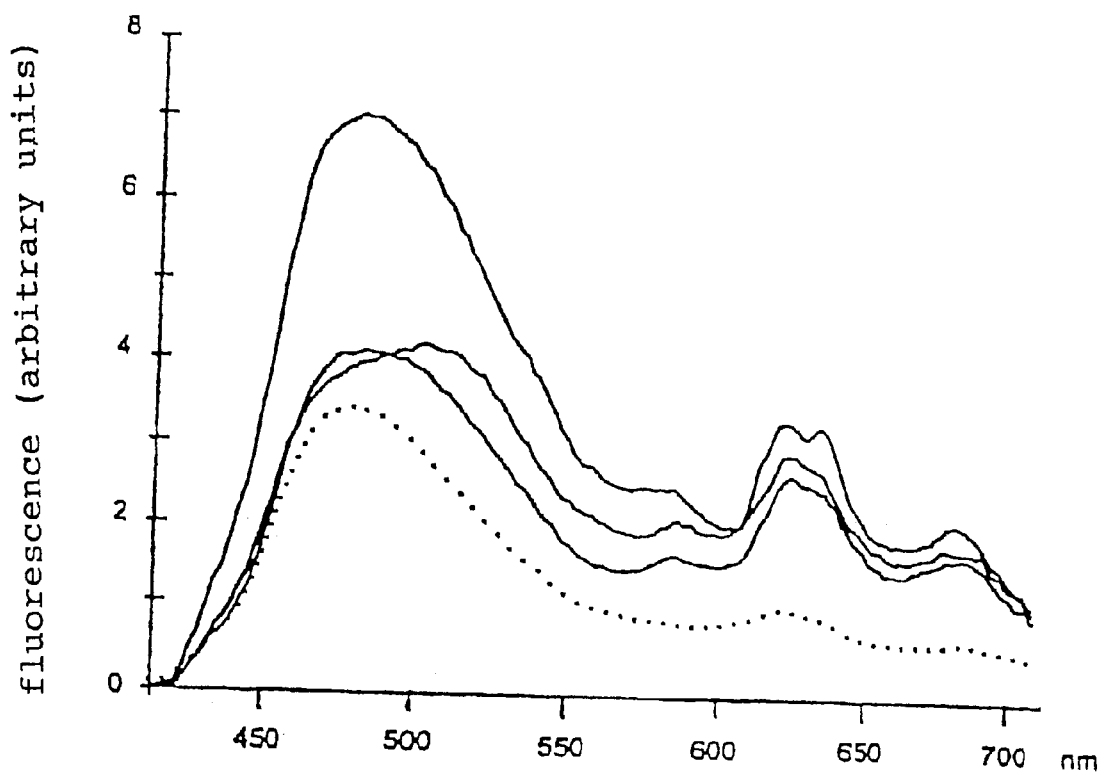
FIG. 7 shows the fluorescence spectra, on the one hand, of a pancreas having chronic pancreatitis and, on the other hand, a healthy pancreas (in broken line)

FIG. 4 shows the corresponding spectra for these clinical situations—namely healthy pancreas, simple edemic pancreatitis, necrotico-hemorrhagic pancreatitis—with moreover the spectrum of an intermediate pancreatitis.

According to a preferred embodiment of the invention, the process consists in forming a fluorescent image of the tissues to be analyzed, on which appears the inflamed zone or zones, by using at least the predetermined number of the florescent intensity characteristic of the endogenous porphyrins for different measurement points in question.

Thus, the process according to the invention permits particularly appreciating, by measuring the fluorescence of the porphyrins, the inflammatory character of an epithelium (skin and mucosa), and establishing a predictive factor of its ultimate development (for example a cheloid scar or the malignant transformation of a pigmented mole).

It also permits detecting inflammations of the epithelia of the pulmonary, digestive, urinary or genital passages by endoscopic measurement of the fluorescence of the porphyrins and establishing a gradation factor of the lesions (for example the esophagus of Barret: inflamed lesion of the esophagus developing progressively to cancer) or following their development (for example, peptic ulcer of the stomach which can develop into healing, a fibrous scar or cancer).

It also permits determining, for example, during the course of a surgical intervention or of a CPRE (choledocho-pancreatic retrograde endoscopy), the level of information of acute or chronic pancreatitis by measurement of the fluorescence of porphyrins in the pancreatic gland or the excretory passages.

In this latter case, the predictive character in terms of gravity of pancreatitis, of the results flowing from the process according to the invention, could be added to the present medical prognostic criteria such as the Ranson score (graduated intensity from 3 to 11) or the pancreatic tomodensitometry (stages D and E).

According to one characteristic of the invention, the luminous excitation is of low intensity, with a power density of delivered energy preferably at most equal to 0.5 W/cm$^2$ (so as not to give rise to local temperature elevation of more than 1° C.).

Moreover, said luminous excitation is preferably constituted by two wavelengths or two spectral bands, namely one of about 590 nm or centered on 590 nm and adapted to excite the porphyrins, and the other of about 400 nm or centered on 400 nm (or if desired about 355 nm), adapted to excite other endogenous chromophores.

The process according to the invention consists more particularly, after the excitation phase, in acquiring, for the same tissues to be analyzed, fluorescence signals in the spectral bands centered, respectively, on about 600 nm (or else about 680 nm) and on about 630 nm and/or 680–690 nm, and, as the case may be, on about 470 nm and/or 510–520 nm, for each of the points to be measured, to form for each above-mentioned spectral band, a fluorescence image from values of fluorescence intensity taken in the spectral band in question for the different points of measurement, carrying out a normalization of the mean values of the intensities of each image obtained, and processing point by point the image or the images obtained for the spectral band or bands centered on about 630 nm and/or about 680–690 nm and using the data contained in the normalized image obtained, for the pass-band centered on 600 nm and, as the case may be, supplemental processing by using the data contained in the image or images obtained for the spectral band or bands centered on about 470 nm and/or about 510–520 nm.

In the frequency bands indicated above, it should be noted that: 470 nm corresponds to the spectral position of the peak of autofluorescence in healthy tissues; 510 nm corresponds to the spectral position of the peak of blue autofluorescence in inflamed tissues; 600 nm (associated with an excitation at 510 nm) corresponds to the autofluorescence in the red spectral band considered as the baseline (background noise) for fluorescence of porphyrins; 630 nm and 690 nm correspond to the spectral positions of the major and minor emission peaks of endogenous porphyrins.

According to one characteristic of the invention, it can preferably be provided to use a normalization factor of a given value for the images collected at 470 nm and/or at 510 nm and another normalization factor of a different value for the images collected at 600 nm and 630 nm and/or 690 nm, the values of these two factors being defined so as to obtain an optimum gradation of the colors or the levels of gray on the final image after processing.

So as to isolate the fluorescence signal generated by the porphyrins, there is carried out a point by point subtraction, or pixel by pixel substraction, of the images of the intensities of the normalized image collected at 600 nm, from those of the normalized image or images collected at 630 and/690 nm.

Moreover, so as to avoid problems of collection of the fluorescence due, among other things, to tissue heterogeneity, one can proceed, after substraction of the normalized image intensities collected at 600 nm, to a point by point division, or pixel by pixel division, of the image intensities or normalized images collected at 630 and/or 690 nm, by the normalized image intensities collected at 470 nm or 510 nm.

As a modification, one can proceed, after subtraction of the intensities of the normalized image collected at 600 nm, to a point by point or a pixel by pixel division of the intensities of the normalized image or images collected at 630 and/or 690 nm by the intensities of the image obtained by point by point substraction of the intensities of the normalized image collected at 510 nm, from those of the normalized image collected at 470 nm, this manner of proceeding improving the contrast between healthy tissues and inflamed tissues.

Thus, according to one preferred embodiment, the operations of image processing can consist more particularly in making the pixel by pixel ratio between the fluorescence image of the endogenous porphyrins ($I_{630}+I_{680}$, after subtraction of the "background noise" taken at 600 nm) and that of the fluorescence of the NADPH ($I_{470}$), which is more intense in the healthy tissues than in the sick tissues.

So as to improve, if necessary, the contrast between the different conditions of the tissue, the process can also use an increase of autofluorescence to 510–520 nm in the process of inflammatory processes, which increase is disclosed by the inventors. In this case, a multiplication of the image ratio $[(I_{630}+I_{680}-\text{background noise})/I_{470}]$ by the image collected at 510–520 nm ($I_{510-520}$) is predetermined.

The object of normalizing the images recorded at the different wavelengths (470, 510–520, 630 and 680, after substraction of noise) is to increase the content of the pixels of the final image resulting from the process described above, so as to increase the dynamic of the final image and thereby to have better localization and visualization of the inflamed portion.

Thanks to the arrangements for image processing mentioned above, the process according to the invention permits obtaining a final image on which is visible only the inflamed zone or zones.

Figure 8:
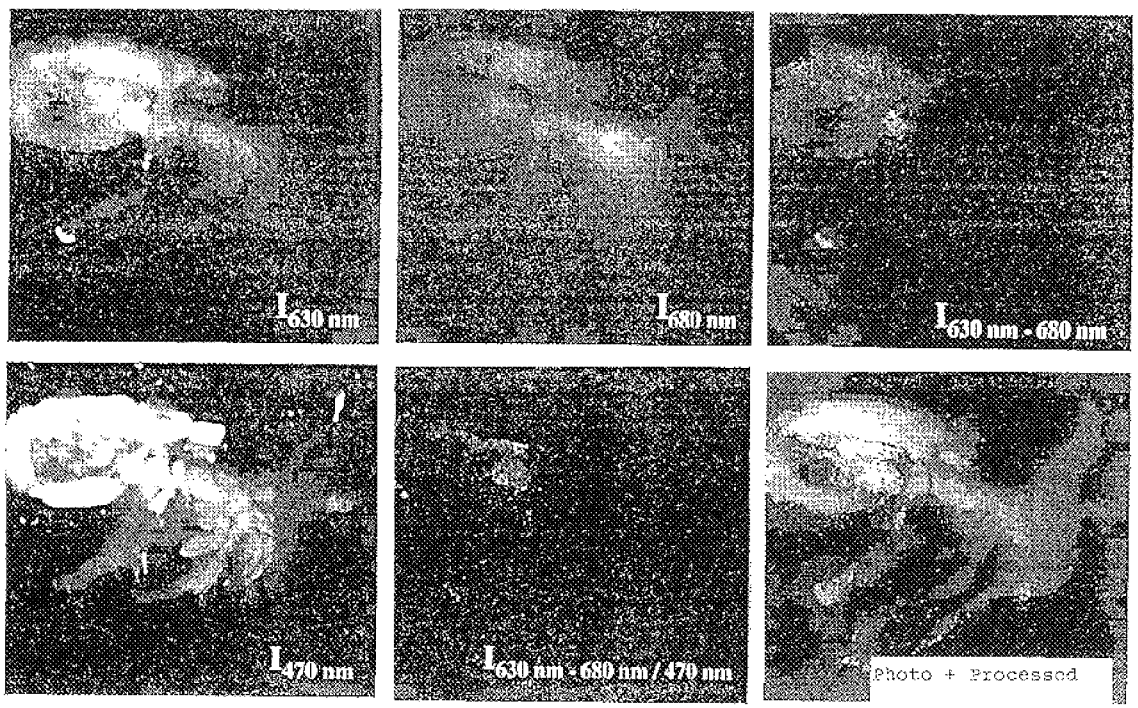
FIGS. 8 and 9 show fluorescence images of a rat pancreas having acute pancreatitis, taken at 630 nm, at 680 nm (replacing the ideal value of 600 nm) and at 470 nm, the images obtained after processing by subtraction and by division point by point according to the process of the invention and the final images used for location (marked Photo+Processed), and, FIG. 10 is a schematic view of a device for practicing the process described above.
Figure 9:
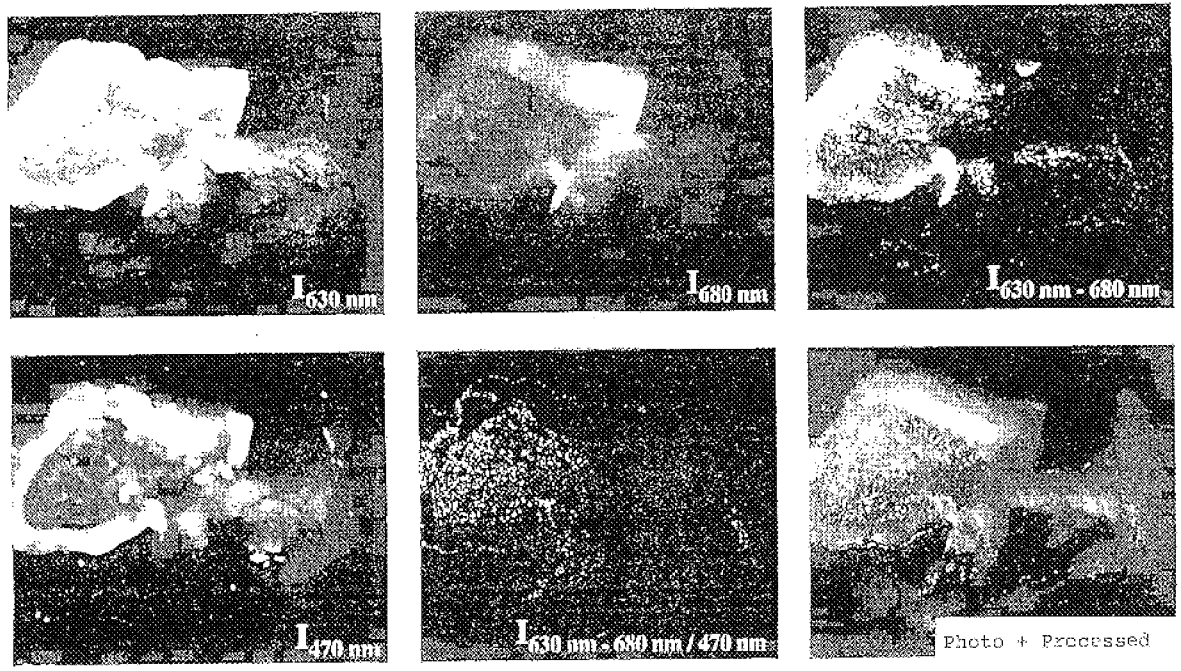

FIGS. 8 and 9 show two examples of localization of zones of inflamed lesions due to acute pancreatitis (weak or moderate) in rat, by the use of a process according to the invention.

These figures therefore show images of fluorescence of the duodenal-pancreatic region, collected by a CCD digital camera. These images have been obtained with laser excitation through pass-band filters permitting selecting fluorescent emissions in the spectral regions characteristic of porphyrins ($I_{630\ nm}$), of autofluorescence in the red ($I_{680\ nm}$) and of autofluorescence in the blue ($I_{470\ nm}$).

The operations of processing images according to the invention permit obtaining first of all the image of the fluorescence of porphyrins properly so-called ($I_{630\ nm-680\ nm}$), then eliminating the contingent output of fluorescence by dividing this latter image by that of the blue autofluroescence (obtained from the marked image $I_{630\ nm-680\ nm/470\ nm}$).

The superposition of this latter image on a normal photographic image permits precisely locating the inflammation zone (Photo+Processed).

The invention also has for its object a device for practicing the process described above, shown in FIG. 10 of the accompanying drawings.

This device is principally constituted by a luminous excitation unit 1 of low intensity in the spectral bands centered on about 400 nm and about 590 nm, a filtering module 2 comprising a set of pass-band filters adapted for selecting specific fluorescenses at the different sought chromophores, a unit 3 for detecting and recording images of the fluorescence of the surface of the tissues examined and, finally, a computing unit 4 for the point by point or pixel by pixel processing of the images collected and the command and management of the assembly of the device, associated with storage and editing means for the images (not shown).

The luminous excitation unit 1 could be comprised either of lasers of suitable wavelength, or of lamps provided with pass-band filters centered on the wavelengths of the mentioned excitation.

Preferably, the unit 3 for detecting and recording images, in false colors, consists of a digital camera CCD.

According to one characteristic of the invention, the excitation unit, the filtering module and the unit for detecting and recording images, are preferably adapted to coact with the optical means used during endoscopy.

Under conditions in which the fluorescent signals will not have much intensity (low excitation or output of fluorescence), it can be provided to add to the CCD camera an image intensifier 5 with a variable gain (typically up to $10^3$).

For use under standard clinical conditions, which is to say in ambient light, this intensifier 5 will be preferentially closable and used in connection with a pulstolated laser 1. Opening the intensifier should be synchronized with the pulses of the excitation laser and the duration of opening less than 100 ns. This will have the advantage on the one hand of avoiding possible saturation of the camera by the ambient light and on the other hand to improve the signal/noise ratio.

If the lifetime of the fluorescence of endogenous porphyrins becomes substantially greater than that of the normal tissue fluorescence, an improvement of the contrast between healthy tissue and inflamed tissue can be obtained by opening the intensifier with a certain delay relative to the excitation for recording the fluorescent images of the porphyrins. There will thus be drastically decreased the contribution of the fluorescence from molecules other than porphyrins and of which the greatest portion of the emission would take place before opening the intensifier.

Thanks to the invention, it is therefore possible to carry out detection and mapping of the inflamed zones of living tissues, as well as an evaluation of the intensity of inflammation, according to a non-invasive evaluation process and without any addition or drugs or injection of chromophores.

Moreover, the process according to the invention preserves the integrity of the patient because it is not necessary to carry out any hypodermic work or removal of tissue, nor to have any direct contact of the apparatus with the tissues to be examined in the course of acquiring data.

Moreover, the use of this process could be used in making either an external examination of the process, or in the scope of the production of an investigative mode already validated, to which no substance harmful to the patient will be added.

Of course, the invention is not limited to the embodiment disclosed and shown in the accompanying drawings. Modifications remain possible, particularly as to the construction of the various elements or by substitution of technical equivalents, without thereby departing from the scope of protection of the invention.

What is claimed is:

1. Process for the detection and mapping of inflamed zones of living tissues, which comprises:
    subjecting the tissues to be analyzed to a luminous excitation with a spectral field;
    acquiring an unprocessed fluorescent signal of endogenous porphyrins at a plurality of measurement points;
    acquiring, for the same tissues to be analyzed, fluorescence signals in the spectral bands centered respectively on about 600 nm and on at least one of about 630 nm and 680–690 nm, and on at least one of about 470 nm and 510–520 nm, for each of the measurement points;
    forming for each spectral band a fluorescence image from values of fluorescence densities taken in the spectral band in question for the different measurement points,
    using a normalization factor of a given value for images collected at at least one of 470 nm and 510 nm and another normalization factor of a different value for images collected at at least one of 600 nm, 630 nm, and 690 nm, the values of these two factors being defined so as to obtain an optimum gradation of the colors or levels of gray on the final image after processing; and
    determining, for each measurement point, the fluorescence intensity for wavelengths characteristic of the endogenous porphyrins.

2. The process according to claim 1, wherein the tissues to be analyzed are from the duodenal-pancreatic region.

3. The process according to claim 1, wherein the fluorescence image or the tissues to be analyzed on which at least one inflamed zone appears is formed by using values of the fluorescence intensity suitable for endogenous porphyrins for the different measurement points.

4. The process according to claim 1, further comprising determining a gradation of the inflammatory character of the zones or lesions by correlation with the fluorescence intensity for the wavelengths characteristic of porphyrins.

5. The process according to claim 1, characterized in that the luminous excitation has a power density of delivered energy at most equal to 0.5 W/cm$^2$, and constituted of two wavelengths or two spectral bands, namely one about 590 nm or centered on 590 nm adapted for the excitation of porphyrins and the other about 400 nm or centered on 400 nm, adapted for the excitation of the other endogenous chromophores.

6. The process according to claim 1, further comprising carrying out a normalization of the mean values of the intensities of each image obtained and carrying out a point by point processing of the image or images obtained for the spectral band or bands centered on at least one of about 630 nm and about 680–690 nm by using the data contained in the normalized image obtained for the pass-band centered on 600 nm, and a supplemental processing by using information contained in the image or images obtained for the spectral band or bands centered on at least one of about 470 nm and about 510–520 nm.

7. The process according to claim 6, further comprising carrying out a subtraction point by point, or pixel by pixel, of the normalized image intensities collected at 600 nm, from those of the normalized image or images collected at at least one of 630 and 690 nm.

8. The process according to claim 7, further comprising carrying out, after subtraction of the normalized image intensities collected at 600 nm, a point by point or pixel by pixel division of the image intensities or of the normalized images collected at at least one of 630 and 690 nm, with intensities of the normalized image collected at 470 nm or 510 nm.

9. The process according to claim 7, further comprising carrying out, after subtraction of the normalized image intensities collected at 600 nm, a point by point or pixel by pixel division of the image densities or the normalized images collected at at least one of 630 nm and 690 nm, by intensities of the image obtained by point by point subtraction of the intensities of the normalized image collected at 510 nm from those of the normalized image collected at 470 nm.

10. The process according to claim 6, further comprising making the ratio, pixel to pixel, between the fluorescence image of the endogenous porphyrins: ($I_{630}+I_{680}$–background noise at 600 nm) and that of a NADPH fluorescence $I_{470}$; and carrying out a multiplication of the obtained image ratio: ($I_{630}+I_{680}$–background noise)/$I_{470}$) by the fluorescence image collected at 510–520 nm.

11. Device for the detection and mapping of inflamed zones of living tissues, which comprises:
    a luminous excitation unit having an intensity equal to at most 0.5 W/cm$^2$, in the spectral bands centered on about 400 nm and on about 590 nm;
    a filtering module comprising a set of pass-band filters adapted for the selection of phosphorescences specific to endogenous porphyrins;
    means for acquiring unprocessed fluorescent signal of the endogenous porphyrins at a plurality of measurement points;
    a unit for detecting and recording images of the fluorescence of the surface of the tissues to be analyzed;
    means for acquiring, for the same tissues to be analyzed, fluorescence signals in the spectral bands centered respectively on about 600 nm and on at least one of about 630 nm and 680–690 nm, and on at least one of about 470 nm and 510–520 nm, for each of the measuring points;
    means for forming for each spectral band a fluorescence image from values of fluorescence densities taken in the spectral band in question for the different measurement points;
    a data processing unit for the point by point or pixel by pixel processing of images collected and the control and management of the assembly of the device, associated with means for storing and editing the images, to detect and map the inflamed zones of the tissues;

said data processing unit using a normalization factor of a given value for images collected at at least one of 470 nm and 510 nm and another normalization factor of a different value for images collected at 600 nm and at at least one of 630 nm and 690 nm, the values of these two factors being defined so as to obtain an optimum gradation of the colors or levels of gray on the final image after processing; and means for determining, for each measurement point, the fluorescence intensity for wavelengths characteristic of the endogenous porphyrins.

12. The device according to claim 11, wherein the unit for detecting and recording images comprises a digital camera CCD, and the excitation unit, the filtering module and the unit for detecting and recording images, are adapted to be operatively associated with optical means used in endoscopy.

13. The device according to claim 12, wherein the digital camera CCD includes an image intensifier with variable gain.

14. The device according to claim 12, further comprising means for carrying out a normalization of the mean values of the intensities of each image obtained and carrying out a point by point processing of the image or images obtained for the spectral band or bands centered on at least one of about 630 nm and about 680–690 nm by using the data contained in the normalized image obtained for the passband centered on 600 nm, and a supplemental processing by using information contained in the image or images obtained for the spectral band or bands centered on at least one of about 470 nm and about 510–520 nm.

15. The device according to claim 14, wherein the data processing unit carries out a subtraction point by point, or pixel by pixel, of the normalized image intensities collected at 600 nm, from those of the normalized image or images collected at at least one of 630 and 690 nm.

16. The device according to claim 15, wherein the data processing unit carries out, after subtraction of the normalized image intensities collected at 600 nm, a point by point or pixel by pixel division of the image intensities or of the normalized images collected at at least one of 630 and 690 nm, with intensities of the normalized image collected at 470 nm or 510 nm.

17. The device according to claim 15, wherein the data processing unit carries out, after subtraction of the normalized image intensities collected at 600 nm, a point by point or pixel by pixel division of the image densities or the normalized images collected at at least one of 630 and 690 nm, by intensities of the image obtained by point by point subtraction of the intensities of the normalized image collected at 510 nm from those of the normalized image collected at 470 nm.

18. The device according to claim 14, wherein the data processing unit effectuates a ratio, pixel to pixel, between the fluorescence image of the endogenous porphyrins: ($I_{630}$+$I_{680}$−background noise at 600 nm) and that of a NADPH fluorescence $I_{470}$, and carries out a multiplication of the obtained image ratio: ($I_{630}$+$I_{680}$−background noise)/$I_{470}$) by the fluorescence image collected at 510–520 nm.

* * * * *